United States Patent [19]

Makino et al.

[11] Patent Number: 4,789,667
[45] Date of Patent: Dec. 6, 1988

[54] EXTERNAL PHARMACEUTICAL COMPOSITION AND METHODS OF USE

[75] Inventors: Yuji Makino; Hideo Matugi; Yoshiki Suzuki, all of Hino, Japan

[73] Assignee: Teijin Limited, Tokyo, Japan

[21] Appl. No.: 771,764

[22] Filed: Sep. 3, 1985

[30] Foreign Application Priority Data

Sep. 3, 1984 [JP] Japan .................... 59-182724

[51] Int. Cl.$^4$ .................... A61K 31/40; A61K 31/56; A61K 31/60; A61K 31/62
[52] U.S. Cl. .................... 514/161; 514/159; 514/177; 514/420; 514/946; 514/947; 514/969
[58] Field of Search ............ 514/159, 161, 969, 946, 514/947, 177, 420

[56] References Cited

PUBLICATIONS

Chem. Abst. (102) 67.401z (1985).
Chem. Abst. (105) 120.767p (1986).

Primary Examiner—Stanley J. Friedman
Attorney, Agent, or Firm—Wenderoth, Lind & Ponack

[57] ABSTRACT

A pharmaceutical composition for external use with the enhanced penetration of a pharmacologically active agent through the skin or mucosa of a warm-blooded animal, said composition comprising (A) a pharmaceutically effective amount of the pharmacologically active agent, and
(B) an optically active or inactive pyroglutamate of the following formula

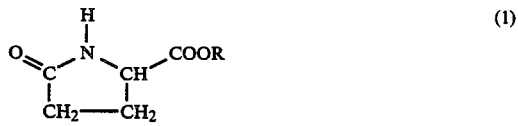

(1)

wherein R represents a linear, branched or cyclic alkyl or alkenyl group having 10 to 14 carbon atoms, as a penentration enhancer.

14 Claims, No Drawings

EXTERNAL PHARMACEUTICAL COMPOSITION AND METHODS OF USE

This invention relates to a novel external pharmaceutical composition. More specifically, it relates to an external pharmaceutical composition containing a specific pyroglutamate as an enhancer for enhancing the penetrability and permeability of a drug through a biological membrane.

Known methods for administering a drug include, for example, oral administration whereby the drug is administered in the form of, for example, a tablet, a capsule, granules, or a syrup to expect absorption through the gastrointestinal tract; topical mucosa administration whereby the drug is administered in the form of, for example, a nasal drop, an eye drop, a buccal preparation or a suppository to except its action in a locality of the mucosa to which it is administered; administration through the mucosa whereby the drug is absorbed through the mucosa to which it is administered to expect its systemic action; topical skin administration whereby it is administered in the form of, for example, an ointment or a cream to expect its action at a locality of the skin to which it is administered; and administration through the skin whereby the drug is absorbed through the skin to which it is administered to expect its systemic action.

By whichever method of administration, the drug administered should penetrate or permeate through a biological membrane. The drug administered orally permeates through the mucosa of the gastrointestinal tract, and gets into the blood or the lymphatic fluid where it is carried to a site of developing its action. The drug administered to the mucosa penetrates through a locality of the mucosa and exhibts its action topically, or migrates to the blood or lymphatic fluid through the mucosa and is carried to a site of developing its action. The drug penetrates or permeates through the mucosa of the nose for the nasal drop, the mucosa of the eye for the eye drop, the mucosa of the oral cavity for the buccal preparation, and the mucosa of the rectum or the mucosa of the vagina for the suppository. The drug administered to the skin penetrates through the skin to exhibit its action topically, or passes into the blood through the skin and is carried to a site of developing its action.

However, there are many drugs which are difficult of penetrating or permeating through a biological membrane and have low bioavailability. Usually, such drugs are administered by injection. Injection is the most accurate method of administration so far as absorption into the body is concerned. But daily injections not only give mental and physical pains to patients, but also may possibly induce a local allergic reaction, eczema, anaphylaxy shock, rupture of a local tissue, etc. It is significant therefore to cause accurate absorption of drugs by methods other than injection.

In view of the foregoing, various enhancers have been investigated which can enhance the penetrability and permeability of drugs having low penetration or permeation through a biological membrane.

In the topical skin administration or the administration through the skin, it is known to use an organic solvent such as dimethyl sulfoxide, dimethylacetamide or propylene glycol, an organic acid ester such as diisopropyl adipate or isopropyl myristate, or a surface-active agent such as sodium laurylsulfate or polyoxyethylene-2-sorbitan monolaurate as an enhancer (W. A. Ritschel, Angew. Chem. Internat. Edit., 1969, pages 699-710). Methods have also been known in which a mixture of a diol compound and an organic acid ester (Japanese Laid-Open Patent Publication No. 81408/1982), or eucalyptol (Japanese Laid-Open Patent Publication No. 15910/1983) is used as an enhancer. These enhancers, however, have one or more defects or troubles. For example, they are malodorous, cause erythema to the skin, or induce necrosis of tissues. It is desired therefore to develop enhancers which are easier to use and have higher safety.

In the topical mucosa administration or the administration through the mucosa, it is known to use cholic acids, saponins, phospholipids, polyoxyethylene alkyl ethers, glycerin fatty acid esters, sorbitan fatty acid esters and polyoxyethylene sorbitan fatty acid esters (Japanese Laid-Open Patent Publication No. 122309/1981), salicylic acid and its derivatives (Japanese Laid-Open Patent Publication No. 122310/1981), ascorbic acid and its derivatives (Japanese Laid-Open Patent Publication No. 138112/1981), acidic amino acids (Japanese Laid-Open Patent Publication No. 138115/1981), citric acid and its derivatives (Japanese Laid-Open Patent Publication No. 138110/1981), and unsaturated fatty acids (Japanese Laid-Open Patent Publication No. 138111/1981) as enhancers. Some of these enhancers, however, damage the mucous membrane of tissues and have insufficient efficacies or other defects, and enhancers which are easier to use and have higher safety have been desired.

Pyroglutamic acid, a kind of amino acid, is contained in large amounts in a human skin, and is one natural moisturizing factor. Natural moisturizing factors adjust moisture in the skin to a suitable amount to maintain the suppleness and elasticity of the skin, and also have many other actions such as protective action, action of buffering acids and alkalies, protective action against bacteria, or respiratory action. Because of these actions, pyroglutamic acid and its salts or esters have previously been used in cosmetics and external dermal drugs. For example, Japanese Laid-Open Patent Publication No. 93,284/1974 states that alkyl esters, cycloalkyl esters and alkenyl esters of pyroglutamic acid are used as additives for cosmetics. This patent document, however, fails to give any description on whether the pyroglutamic acid esters have an effect of enhancing the penetrability or permeability through the skin of a substance to be present together with them, for example, a drug.

U.S. Pat. Nos. 4,064,238 and 3,920,814 state that when pyroglutamic acid, its salts, its $C_1$–$C_6$ alkyl esters or its glycerin ester is administered orally or intravenously together with an antibiotic, the effect of the antibiotic is enhanced. The patents, however, do not state whether pyroglutamic acid or its derivatives mentioned have an effect of enhancing the penetrability or permeability of drugs through the skin.

U.S. Pat. No. 3,836,665 (corresponding to West German OLS No. 2,102,172 and Japanese Laid-Open Patent Publication No. 14172/1972) describes a topical dermatological composition for cosmetic sebaceous gland secretioninhibiting treatment or thrapeutic antiphlogistic treatment of the skin consisting essentially of an inert dermatological carrier and from 0.1 to 10% by weight, based on total weight of the composition, of a compound of the formula

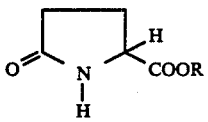

wherein R is straight or branched alkyl of 8 to 30 carbon atoms. Since this composition is used for treating the skin itself, the specification of this U.S. Patent neither describes nor suggests that a drug penetrates through the skin. The U.S. Patent states that pyroglutamates of the above formula in which R has 16 to 20 carbon atoms are preferred, and specifically discloses a dermatological agent comprising hexadecyl ($C_{16}$ alkyl) pyroglutamate and a drug. From the description of the U.S. Patent, it appears that this dermatological agent exhibits an effect of inhibiting sebaceous gland excretion, anti-inflammatory activity, anti-proliferative activity, dandruff-preventing activity, a capillary stabilizing effect, local anethetizing activity, skin protecting activity and skin moisturizing activity by the action of the glutamate itself.

Investigations of the present inventors, however, have shown that the above dermatogoligical agent does not substantially enhance the penetration of drugs through the skin.

British Patent No. 1,567,496 (corresponding to West German OLS No. 2,707,814 and Japanese Laid-Open Patent Publication No. 122,6437/1977) describes a composition for the protection and treatment of the skin comprising at least one suitable carrier and at least one compound having the general formula

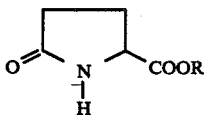

wherein R is a terpene alcohol selected from the group consisting of menthol, borneol, geraniol and citronellol. The above composition is also used to protect and treat the skin, and the British Patent neither describes nor suggests that a drug penetrates through the skin. From the description of the British specification, it appears that this composition, by the action of the pyroglutamate of the above formula itself, has a stabilizing effect on the capillary walls, anti-inflammatory activity and a regulating effect on sebaceous gland secretion. The description of the British Patent therefore suggests that the above pyroglutamates have the same actions as the pyroglutamates described in the above-cited U.S. Pat. No. 3,836,665.

U.S. Pat. No. 4,434,159 and European Patent No. 37,943 describe a pharmaceutical composition for intrarectal administration in which a drug substantially unabsorbable through the mucosa of the rectum is rendered absorbable through the rectal mucosa with the help of an absorption aid. The U.S. Patent discloses pyroglutamic acid or its salts as an example of the absorption aid, but neither describes nor suggests esters of pyroglutamic acid. European Laid-Open Patent Publication No. 123,948 and the corresponding U.S. patent application Ser. No. 595,835 filed by the same applicant as the present one describes a pharmaceutical composition for external use with the enhanced penetration of a pharmacologically active agent through the skin or mucosa of a warm-blooded animal, said composition comprising (A)' a pharmaceutically effective amount of the pharmacologically active agent, and (B)' a penetration enhancer of the following formula (1)'

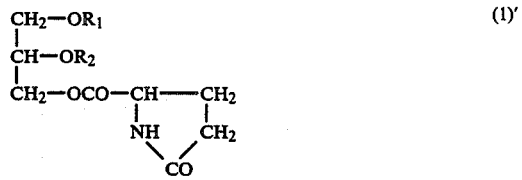

wherein $R_1$ and $R_2$ are identical or different and each represents a hydrogen atom, an alkyl group having 1 to 25 carbon atoms, an alkenyl group having 2 to 25 carbon atoms, a ($C_{1-24}$ alkyl)carbonyl group or a ($C_{2-24}$ alkenyl)carbonyl group, provided that $R_1$ and $R_2$ are not hydrogen atoms at the same time, or $R_1$ and $R_2$, taken together, may form a group of the following formula (a)

in which $R_3$ and $R_4$ are identical or different and each represents a hydrogen atom, an alkyl group having 1 to 24 carbon atoms or an alkenyl group having 2 to 24 carbon atoms. The composition is characterized by using the penetration enhancer of formula (1)' above.

It is an object of this invention is to use a certain optically active or inactive pyroglutamate for enhancing the penetration of a pharmacologically active agent through the skin or mucosa of a warm-blooded animal.

Another object of this invention is to provide a pharmaceutical composition for external use comprising a compound which is novel as a penetration enhancer and has the action of enhancing the penetration of a pharmacologically active agent through the skin or mucosa of a warm-blooded animal.

Another object of this ivnention is to provide a pharmaceutical composition for external use comprising a pharmacologically active agent together with a compound which is novel as a penetration enhancer and has the ability to enhance the penetration of the pharmacologically active agent through the skin or mucosa of a warm-blooded animal when used externally.

Another object of this invention is to enable a pharmacologically active agent being incapable or difficult of penetrating through the the skin or mucosa of a warm-blooded animal, for example a pharmacologically active agent having relatively high hydrophilicity or a relatively high molecular weight, to penetrate through the skin or mucosa by using a compound having the above action and being novel as a penetration enhancer and to exhibit its desirable pharmacological activity.

Another object of this invention is to provide a pharmaceutical composition for external use comprising a certain pyroglutamic acid ester which shows higher penetration enhancing ability than the glycerin ester of pyroglutamate previously proposed by the present inventors.

Another object of this invention is to use a pharmacologically active agent, which when administered orally or by injection, is decomposed in the digestive tract, etc. or exhibits an undesirable physiological action, together with a compound having the aforesaid action and being novel as a penetration enhancer, and to develop the desirable activity of the pharmacologically active agent to an utmost extent while avoiding the aforesaid undesirable results.

Another object of this invention is to provide a pharmaceutical composition for external use comprising a pharmacologically active agent capable of exhibiting its pharmacological activity when externally used and a compound having the aforesaid action and being novel as a penetration enhancer, said composition being capable of developing a pharmacological activity equivalent to that of the pharmacologically active agent more rapidly or with a smaller amount of the pharmacologically active agent by the conjoint use of the penetration enhancer.

Another object of this invention is to provide a pharmaceutical composition for external use comprising a pharmacologically active agent which tends to lose its activity by being metabolized in the liver and cannot maintain its minimum effective blood level over an extended period of time when internally administered and which when used together with a compound having the aforesaid activity and being novel as a penetration enhancer, maintains its minimum effective blood level over an extended period of time and effectively exhibits a systemic action. This composition is provided by utilizing the fact that unlike a pharmacologically active agent which is absorbed from the digestive tract and carried by the blood stream by internal administration, a pharmacologically active agent which is absorbed and carried by the blood stream by external administration returns to the heart before it passes through the liver and therefore takes a longer period of time until passage through the liver.

Another object of this invention is to provide a pharmaceutical composition for external use comprising a pharmacologically active agent which tends to lose its activity by being metabolized in the liver but which when applied externally together with a compound having the aforesaid activity and being novel as a penetration enhancer by utilizing the aforesaid blood stream in vivo, can be directly caused to act topically in an effective amount on a particular site at which it is desired to exhibit its pharmacological action.

Another object of this invention is to provide a pharmaceutical composition for external use comprising a nontoxic and safe pyroglutamate which is novel as a penetration enhancer, said composition being based on the present inventors' discovery that the above penetration enhancer compound enhances the penetration of a pharmacologically active agent when used together.

Further objects of this invention along with its advantages will become apparent from the following description.

The above objects and advantages of this invention are achieved in accordance with this invention by a pharmaceutical composition for external use with the enhanced penetration of a pharmacologically active agent through the skin or mucosa of a warm-blooded animal, said composition comprising (A) a pharmaceutically effective amount of the pharmacologically active agent, and (B) an optically active or inactive pyroglutamate of the following formula

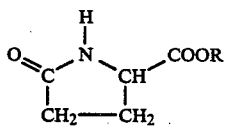

wherein R represents a linear, branched or cyclic alkyl or alkenyl group having 10 to 14 carbon atoms, as a penetration enhancer.

The pyroglutamate used as a penetration enhancer in the present invention is represented by the above formula (1).

In formula (1), R represents a linear, branched or cyclic alkyl or alkenyl group having 10 to 14 carbon atoms. Pyroglutamates of formula (1) in which R is an alkyl or alkenyl group having 9 or less carbon atoms or 15 or more carbon atoms hardly enhance the penetration of a pharmacologically active agent through the skin or mucosa although no clear reason can now be assigned to it.

Examples of the linear or branched alkyl group having 10 to 14 carbon atoms include decyl, undecyl, dodecyl, tridecyl, tetradecyl, 2-ethyl-decyl, 9-ethyl-decyl, 2-ethyl-dodecyl and 11-ethyl-dodecyl groups.

Examples of the linear or branched alkenyl group having 10 to 14 carbon atoms include 4-decenyl, 9-decenyl, 4-dodecenyl, 5-dodecenyl, 9-dodecenyl, 4-tetradecenyl, 5-tetradecenyl, 9-tetradecenyl, 9-ethyl-4-decenyl, 4-ethyl-9-dodecenyl, geranyl, citronyl, linanyl, and neryl groups.

Examples of the cyclic alkyl or alkenyl group having 10 to 14 carbon atoms are menthyl, bornyl, and terpenyl groups.

Of the compounds of formula (1), those in which R is a linear or branched alkyl or alkenyl group having 12 to 14 carbon atoms, especially a linear or branched alkyl group having 12 carbon atoms, are preferred.

The compounds of formula (1) may be optically active or optically inactive with respect to the asymmetric carbon atom to which the carboxylate group is bonded, and are used preferably in L-form or DL-form.

Examples of the compounds of formula (1) are listed below.

Compounds of formula (1) in which R is a linear or branched alkyl group having 10 to 14 carbon atoms (102) Decyl DL-pyroglutamate,
(104) Undecyl DL-pyroglutamate,
(106) Dodecyl DL-pyroglutamate,
(108) Tridecyl DL-pyroglutamate,
(110) Tetradecyl DL-pyroglutamate,
(112) Decyl L-pyroglutamate,
(114) Undecyl L-pyroglutamate,
(116) Dodecyl L-pyroglutamate,
(118) Tridecyl L-pyroglutamate,
(120) Tetradecyl L-pyroglutamate,
(122) Decyl D-pyroglutamate,
(124) Undecyl D-pyroglutamate,
(126) Dodecyl D-pyroglutamate,
(128) Tridecyl D-pyroglutamate,
(130) Tetradecyl D-pyroglutamate,
(132) 2-Ethyldecyl L-pyroglutamate,
(134) 9-Ethyldecyl L-pyroglutamate,
(136) 2-Ethyldodecyl L-pyroglutamate,
(138) 11-Ethyldodecyl L-pyroglutamate.

Compounds of formula (1) wherein R is a linear or branched alkenyl group having 10 to 14 carbon atoms (202) 4-Decenyl DL-pyroglutamate,
(204) 4-Dodecenyl DL-pyroglutamate,
(206) 4-Tetradecenyl DL-pyroglutamate,
(208) Geranyl DL-pyroglutamate,
(210) Citronyl DL-pyroglutamate,
(212) Linanyl DL-pyroglutamate,
(214) 4-Decenyl L-pyroglutamate,
(216) 4-Dodecenyl L-pyroglutamate,
(218) 4-Tetradecenyl L-pyroglutamate,
(220) 9-Dodecenyl L-pyroglutamate,
(222) Geranyl L-pyroglutamate,
(224) Citronyl L-pyroglutamate,
(226) Linanyl L-pyroglutamate.

Compounds of formula (1) wherein R is a cyclic alkyl or alkenyl group having 10 to 14 carbon atoms (302) Menthyl DL-pyroglutamate,
(304) Bornyl DL-pyroglutamate,
(306) Terpenyl DL-pyroglutamate,
(308) Menthyl L-pyroglutamate,
(310) Bornyl L-pyroglutamate,
(312) Terpenyl L-pyroglutamate.

The pyroglutamate of formula (1) can be produced by methods known per se, for example U.S. Pat. No. 3,836,665. Specifically, it can be produced by reacting pyroglutamic acid or its reactive derivative such as a halide or anhydride with an alcohol of the following formula $$R-OH \quad (2)$$

wherein R is the same as defined in formula (1), (1st variation); or by heating a compound represented by the formula

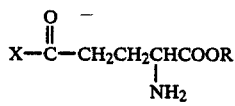 (3)

wherein X is OH, Cl, Br or $C_{1-6}$ alkoxy and R is the same as defined in formula (1),
to cyclize it intramolecularly (2nd variation).

The pyroglutamates of formula (1) in accordance with this invention are novel as a penetration enhancer which enhance the penetration of pharmacologically active agents through the skin or mucosa of a warm-blooded animal.

Since the pharmaceutical composition for external use in accordance with this invention comprising the pyroglutamate of formula (1) has a great ability to permit a pharmacologically active agent to penetrate the skin or mucosa, the present invention is applicable to pharmacologically active agents being incapable or difficult of penetrating the skin or mucosa, such as pharmacologically active agents having relatively high hydrophilicity or a relatively high molecular weight.

Furthermore, according to the composition of this invention, even those pharmacologically active agents which are known to penetrate the skin or mucosa can exhibit their pharmacological activities more rapidly after application, or can exhibit required pharmacological activity in smaller dosages.

When the composition of this invention is applied to pharmacologically active agents which are known to be unable to exhibit sufficient pharmacological activity in external use and have to be administered orally or by injection but which when administered orally or by injection, tend to undergo decomposition in the digestive tract, etc. or develop an undesirable physiological action, it is possible to have these agents exhibit sufficient pharmacological activities while circumventing the aforesaid undesirable results.

The composition of this invention is applicable therefore to a very large number of pharmacologically active agents including, for example, anti-inflammatory agents, agents for the circulatory system, antimicrobial agents, anti-ulcer agents, hormones, analgesic agents, anti-cancer agents, antiemetic agents, anti-allergic agents, agents for the respiratory system, agents for the central nervous system, agents for the peripheral nervous system, biologicals and agents for the metabolic system.

More specific examples of the pharmacologically active agents that can be used in accordance with this invention are shown below.

The anti-inflammatory agents include, for example, nonsteroidal agents such as salicyclic acid, aspirin, acetoaminophene, aminopyrine, antipyrine, oxyphenbutazone, sulpyrine, indomethacin, sodium diclofenac, ibuprofen, slindac, naproxen, ketoprofen, etofenamate, salicylamide, salsalate, triethanolamine, salicylate, apazone, fulfenamic acid, meclophenamic acid, demecolcine, allopurinol, oxypurinol, ibufenac, fenbufen, diflunisal, alcrofenac, phenylbutazone, mefenamic acid, fenoprofen, bendazac, piroxicam and flurbiprofen; and steroidal agents such as amcinonide, prednisolone valerate acetate, diflucortolone, valerate, betamethasone valerate, betamethasone acetate, dexamethazone acetate, betamethasone dipropionate, dexamethasone, triamcinolone acetonide, hydrocortisone, flumethasone pivalate, fluocinonide, fluocinolone acetonide, fluorometholone, fluodroxycortide, prednisolone, clobetasol propionate, beclometasone dipropionate, betamethasone, methylprednisolone, methylprednisolone acetate, and hydrocortisone butyrate.

The agents for the circulatory system include, for example, antihypertensive agents such as Rauwolfia alkaloids (e.g., reserpin and rescinnamine), clonidine, prazosin, dihydroergotamine mesylate, meticrane, methyldopa, guanethidine, betanidine and prostaglandins; vasodilators such as efloxate, etafenone, oxyfedrine, carbochromen, dilazep, diltiazem, trimetazidine, verapamil, pentaerythritol tetranitrate, dipyridamole, isosorbide dinitrate, trapidil, nitroglycerin, nifedipine, prenylamine, molsidomine, trotrolnitrate phosphate, inositol hexanicotinate, isoxsuprine, nylidrin, nicamate citrate, cyclandelate, cinnarizine, nicotinic alcohol and hepronicate; anti-arrhythmic agents such as acebutolol, alprenolol, indenolol, oxprenolol, carteolol, bucumolol, bufetolol, bupranolol, propranolol and pindolol; and anticoagulants such as heparin, chondroitin sulfate and prostaglandins.

The antimicrobial agents include, for example, penicillin-type antibiotics such as penicillin G, penicillin V, methicillin, oxacillin, cloxacillin, ampicillin, hetacillin, cyclacillin, amoxycillin, carbenicillin and sulbenicillin; cepharosporin-type antibiotics such as cephaloridin, cephalothin, caphazolin, cephaloglycin and cephalexin; aminoglycoside-type antibiotics such as streptomycin, kanamycin, dibekacin, gentamicin and fradiomycin; tetracycline-type antibiotics such as oxytetracycline, tetracycline, dimethylchlorotetracycline, doxycycline and minocycline; macrolide-type antibiotics such as erythromycin, leucomycin, josamycin and spiramycin; lincomycin-type antibiotics such as lincomycin and clindamycin; other antibiotics such as chloramphenicol, novobiocin, micamycin, bacitracin, gramicidin, gramicidin S, viomycin, capreomycin, cycloserin, enviomycin, rifampicin, nystatin, pentamycin, trichomycin, amphotericin B, griseofulvin, variotin, pyrrolnitrin, nitrofurantoin, thiabendazole, cephamycin, phosphonomycin, N-formidoylthienamycin monohydrate, and 1-ethyl-6-fluoro-1,4-dihydro-4-oxo-7-(1-piperazinyl)-3-quinolinecarboxylic acid; external sulfur drugs such as acetyl mafenide, sulfadiazine, silver sulfadiazine, sodium sulfamethoxazal, sulfisomidine, and sodium sulfisomidine; and other drugs such as iodine, povidoneiodine, diiodohydroxyquine, benzalkonium chloride, benzethonium chloride, methylrosaniline chloride, hexachlorophene, chlorohexidine hydrochloride, benzoyl peroxide, tolunaftate, acyclovir and 5-iodo-2'-deoxyuridine.

The anti-ulcer agents include, for example, prostaglandins such as 17,20-dimethyl-6-oxoprostaglandin-$E_1$ methyl ester, 15-methyl-prostaglandin $E_2$, 16-methyl-16-hydroxy-15-dehydroxyprostaglandin $E_1$ methyl ester, 7-thiaprostaglandin $E_1$ methyl ester, and 17,20-dimethyl-7-thiaprostaglandin $E_1$ methyl ester.

The hormones include, for example, insulin, angiotensin, vasopressin, felypressin, protirelin, gonadotropin-releasing hormone, corticotropin, prolactin, somatotropin, thyrotropin, luteinizing hormone, calcitonin, catacalcin, kallikrein, parathyrin, glucagon, oxytocin, gastrin, secretin, serum gonadotropin, and sex hormones such as estrogen, estradiol, testosterone, and progesterone.

The analgesic agents include, for example, azapropazone, benzydamine, phenacetin, butylon, mepirizole, triaromide and migrenin.

The anti-cancer agents include, for example, 5-fluorouracil, 6-mercaptopurine, mycophenolic acid, methotrexate, bleomycin, mitomycin C, carbazilquinone, actinomycin C, carzinophlin, daunorubicin, doxorubicin, neocarzinostatin, chromomycin $A_3$, L-asparaginase, picibanil, podophyllotoxin, vinblastine and vincristine.

Examples of the antiemetic agents include pipamazine, chlorpromazine and dimenhydrinate.

Examples of the anti-allergic agents are cycloheptadine hydrochloride and cinnarizine.

Antiasthma agents such as disodium cromoglycate may be cited as examples of the agents for the respiratory system.

Examples of the agents for the central nervous system include diazepams such as flurazepam, nimetazapam, nitrazepam and estazolam, and scoporamin.

The agents for the peripheral nervous system include, for example, benzocain, procaine, propoxycaine, dibucanine, lidocaine, mepivacaine, bupivacaine and tetracaine.

The biologicals include, for example, enzymes such as trypsin, papain, protease, lysozyme, streptokinase, plasmin, urokinase, hyaluronidase, α-chymotrypsin, serratiopeptidase, bromelain, and seaprose; microbial cell extracts such as PSK; interferon; and interleukin.

The agents for the metabolic system include, for example, fat-soluble vitamins such as 1,25-dihydroxyvitamin $D_3$, 1α-hydroxyvitamin $D_3$, 1,24-dihydroxyvitamin $D_3$, 24,25-dihydroxyvitamin $D_3$, 1α,25-dihydroxyvitamin $D_3$-26,23-lactone, and 25-hydroxyvitamin $D_3$-26,23-lactone.

It should be understood that the above-cited drugs are only some examples of pharmacologically active @agents which can be applied to the composition of this invention, because almost all drugs do not penetrate, or have difficulty in penetrating, the skin or mucosa.

Among the above-cited drugs, salicyclic acid, nitroglycerin, isosorbide dinitrate, pentaerythritol tetranitrate, testosterone, progesteron, estrogen, estradiol, and scoporamin are known to be absorbed through the skin or mucosa. According to the present invention, the penetration of even these drugs can be enhanced. Hence, their pharmacological activity can be developed more rapidly after application, and the amount of these drugs to be applied can be decreased.

Furthermore, those drugs which have previously been administered orally but with undesirable side-effects such as great tendency to induce ulcer formation on the gastric wall, for example anti-inflammatory agents such as indomethacin, salicyclic acid, aspirin and phenylbutazone or anti-cancer agents such as 5-fluorouracil and 6-mercaptopurine can effectively develop their desirable pharmacological activities with inhibited side-effects if applied to the skin or mucosa as the pharmaceutical composition of this invention.

Furthermore, those drugs which have previously been administered orally but with susceptibility to decomposition in the digestive tract or to metabolization and have had difficulty in developing their pharmacological activities sufficiently, for example nitroglycerin, isosorbide dinitrate, nifedipine, acebutorol, alprenolol, propranolol, insulin, testosterone, calcitonin, prostaglandins, interferon and interleukin can exhibit their pharmacological activities sufficiently while inhibiting their decomposition or metabolization when applied to the skin or mucosa as the pharmaceutical composition of this invention. Since the penetration enhancer of formula (1) in accordance with this invention enhances the penetration of a drug from the skin or musoca, it can inhibit the decomposition of the drug in the digestive tract to the greatest possible extent, and also prolong the time which elapses until the drug is metabolized in the liver, thus maintaining the minimum effective level in the blood over an extended period of time.

Among the above-exemplified drugs, cepharosporin-type antibiotics such as cephaloridin, cephalothin and cephazolin and penicillin-type antibiotics such as carbenicillin and sulbenicillin have not been able to penetrate the skin or mucosa because of their especially high molecular weights or high hydrophilicity. By formulating such antibiotics into pharmaceutical compositions for external application in accordance with this invention, these drugs can penetrate the skin or mucosa to an extent that their pharmacological activities can be effectively exhibited.

The above and other advantages of the pharmaceutical compositions for external use in accordance with this invention will become apparent from the following Examples.

The term "external" or "externally", as used in the present specification and the appended claims, expresses the application of a drug or a composition containing it to the skin or a warm-blooded animal or the mucosa of a specified site of a warm-blooded animal such as the mucosa of the oral cavity, the mucosa of the nasal cavity, the mucosa of the rectum or the mucosa of the vagina. Accordingly, the term "external" or "externally" is used irrespective of whether the pharmacological action of a drug in the composition of this invention is developed topically or systemically. As will be clear from the specific examples of the drugs given hereinabove and their descriptions, the compositions of this invention include not only those which develop a topical action but also those which develop a systemic action.

The composition of this invention may comprise an ordinary pharmaceutically acceptable carrier or adjuvant in addition to the pharmacologically active agent and the penetration enhancer of formula (1).

In the composition of this invention, the amount of the pyroglutamate vary depending upon the type and amount of the drug and the desired form into which the composition is to be molded. For example, if a peptide hormone such as calcitonin or insulin is used as the drug and the composition is to be formulated into a suppository, the amount of the pyroglutamate used is preferably about 0.1 to 200 times the weight of the drug. If a prostaglandin is used as the drug and the composition is to be formulated into an ointment, the amount of the pyroglutamate used is about 10,000 to 500,000 times, preferably about 10,000 to 100,000 times the weight of the drug. If a nonsteroidal anti-inflammatory agent such as indomethacin is used as the drug and the composition is to be formulated into an ointment, the amount of the pyroglutamate used is about 0.1 to 100 times the weight of the drug. When other drugs are used, the amount of the pyroglutamate is determined depending upon the type of the drug and the desired form into which the composition is to be molded.

The pharmaceutical composition of this invention may be in the form of a solution, an emulsion, a suspension, a semisolid, a powder, a solid of a fixed shape such as a tablet, or a film depending upon the pharmaceutically acceptable carrier or adjuvant. Accordingly, the composition of this invention can be prepared into a suitable form depending upon the site of application, etc.

The forms of the composition of this invention may be classified as shown below according to the classification in the art. The composition in the form of a solution includes solutions, aerosols, and capsules having a gelatin shell. The composition in the form of a suspension includes suspensions, lotions, aerosols, and capsules having a gelatin shell. The semisolid composition includes ointments, creams, liniments, pastes and gels. The powdery composition includes powders, capsules and granules. The composition to be molded into a definite shape includes tablets, and body temperature-soluble solid preparations. The composition in the form of a film includes plasters, tapes and films.

The pharmaceutically acceptable carrier or adjuvants used in the composition of this invention is known to the art. Suitable carriers or adjuvants may be used depending upon the desired form of the composition. For example, beeswax, vegetable oils, lanolin, boric acid and white Vaseline are used for ointments. Oils and fats, waxes, higher fatty acids, higher alcohols, etc. are used for creams. Ethanol, glycerol, butylene glycol, etc, are used for lotions. Tragacanth, gum arabic, sodium alginate, gelatin, methyl cellulose, CMC, etc. are usually used for suspensions. For body temperature-soluble solid preparations, Vaseline, oils and fats such as cacao butter, palm oil, coconut oil, or fractionated coconut oil, etc. are normally used. Methyl cellulose, hydroxypropyl cellulose, hydroxypropyl methyl cellulose, crystalline cellulose, starch, etc. are used for tablets and granules. For films, hydroxypropyl cellulose, methyl cellulose, polyvinyl pyrrolidone, polyvinyl alcohol, etc. may be used.

The composition of this invention comprising such a carrier or adjuvant may be produced by known methods usually practiced in the art.

Generally, when a drug is applied to the skin as an external agent, not all of the drug contained in the external agent penetrates the body through the skin. In view of this, it is surprising to note that according to the composition of this invention, even those drugs which have heretofore been administered orally or by injection can sufficiently exhibit their expected effects by using them in amounts which do not greatly differ from the known dosages.

The composition of this invention contains the penetration enhancer of formula (1) in an amount of 0.2 to 25% by weight, preferably 0.5 to 12% by weight, based on the total weight of the composition.

It will be seen from the foregoing that the present invention also provides a method of administering a pharmacologically active agent to a warm-blooded animal, which comprises externally applying (A) a pharmaceutically effective amount of the pharmacologically active agent in combination with (B) a penetration enhancer of the above formula (1) to the surface of the skin or mucosa of the warm-blooded animal to enhance the penetration of the pharmacologically active agent through the skin or mucosa.

The mucosa mentioned above may be that of the rectum, oral cavity, nasal cavity or vagina of the warm-blooded animal.

In accordance with the method of this invention, the pharmacologically active agent may be applied to one or several sites of the skin or mucosa, and once or several times a day.

Preferably, the pharmacologically active agent is applied to the skin or mucosa as the pharmaceutical composition for external use in accordance with this invention.

The following Examples illustrate the present invention more specifically.

In these examples, the enhanced penetration or permeation of drugs through the skin of rats was determined by applying an ointment containing a drug to the abdomen of the rats and measuring the concentration of the drug in the blood. Furthermore, the enhance penetration or permeation of a drug through the rectum of rats or rabbits was determined by inserting a suppository containing the drug into the rectum of the rats or rabbits, and measuring the pharmacological effect of the drug. In addition, the enhanced penetration or permeation of a drug through a biological membrane was determined by placing an egg shell membrane within a diffusion cell and measuring the amount of the drug diffused through the membrane.

All parts in these examples are by weight unless otherwise specified.

EXAMPLES 1-14

An ointment was prepared from 1 part of indomethacin, 10 parts of each of the various pyroglutamates shown in Table 1 (Examples 1 to 14), and 89 parts of a gel ointment base (composed of 1 part of Carbopol 934, 132 parts of propylene glycol, 30 parts of ethanol, 1 part of diisopropanolamine and 56 parts of water). The hair in the abdomen of each rat (body weight about 250 g) was removed by an electric hair clipper, and 100 mg of the resulting ointment was coated by a finger tip on a circular area having a diameter of 4 cm on the abdomen. After the lapse of a certain period of time, the blood was drawn from the tail portion of the rat, and the concentration of indomethacin in the blood was periodically determined by high performance liquid chromatography.

For comparison, ointments composed of 1 part of indomethacin, 10 parts of the various pyroglutamates shown in Table 1 (Comparisons 1 to 14) and 89 parts of the gel ointment base, and an ointment (Comparison 15) composed of 1 part of indomethacin and 99 parts of the gel ointment base without the inclusion of the pyroglutamate were prepared. These comparative ointments were applied to the abdomens of rats, and the concentration of indomethacin in the blood was measured, in the same way as above.

The results are shown in Table 1. It is seen that the absorption of indomethacin from the ointments of Examples 1 to 14 (the compositions of this invention) was better than the comparative ointments. During the application of the compositions of this invention and the other ointments, no change in the skin such as erythema was observed at the site of administration.

After the final drawing of the blood, the rats were killed, and the stomachs were extracted. The stomachs were cut open to examine the formation of ulcer. No formation of ulcer in the stomachs was observed both in the case of using the compositions of the invention and the other ointments.

EXAMPLES 15-28

An ointment was prepared from 1 part of nifedipine, 10 parts of each of the various pyroglutamates shown in Table 2 (Examples 15 to 28), and 89 parts of a gel ointment base (composed of 1 part of Carbopol 934, 12 parts of propylene glycol, 30 parts of ethanol, 1 part of diisopropanolamine and 56 parts of water). The hair in the abdomen of each rat (body weight about 250 g) was removed by an electric hair clipper, and 100 mg of the resulting ointment was coated by a finger tip on a circular area having a diameter of 4 cm on the abdomen. After the lapse of a certain period of time, the blood was drawn from the tail portion of the rat, and the concentration of nifedipine in the blood was periodically determined by high performance liquid chromatography.

For comparison, ointments composed of 1 part of nifedipine, 10 parts of the various pyroglutamates shown in Table 2 (Comparisons 16 to 30) and 89 parts of the gel ointment base, and an ointment (Comparison 31) composed of 1 part of nifedipine and 99 parts of the gel ointment base without the inclusion of the pyroglutamate were prepared. These comparative ointments were applied to the abdomens of rats, and the concentration of nifedipine in the blood was measured, in the same way as above.

The results are shown in Table 2. It is seen that the absorption of nifedipine from the ointments of Examples 15 to 28 (the compositions of this invention) was better than the comparative ointments. During the application of the compositions of this invention and the other ointments, no change in the skin such as erythema was observed at the site of administration.

TABLE 1

| | | Penetration enhancer | | Concentration of indomethacin in the blood ($\mu$g/ml) | | | |
|---|---|---|---|---|---|---|---|
| | | | | 3 hrs. | 6 hrs. | 9 hrs. | 24 hrs. |
| Example | 1 | Compound | (112) | 0.75 | 1.54 | 2.40 | 1.77 |
| " | 2 | " | (114) | 0.71 | 1.88 | 2.25 | 1.89 |
| " | 3 | " | (116) | 0.62 | 1.97 | 2.94 | 1.88 |
| " | 4 | " | (118) | 0.59 | 1.75 | 2.41 | 1.90 |
| " | 5 | " | (120) | 0.58 | 1.86 | 2.25 | 1.63 |
| " | 6 | " | (102) | 0.69 | 1.36 | 1.44 | 1.35 |
| " | 7 | " | (104) | 0.65 | 1.76 | 2.08 | 1.53 |
| " | 8 | " | (106) | 0.71 | 1.87 | 1.80 | 1.42 |
| " | 9 | " | (108) | 0.40 | 1.09 | 1.89 | 1.42 |
| " | 10 | " | (110) | 0.55 | 1.74 | 1.72 | 1.29 |
| Comparison | 1 | L-Pyroglutamic acid | | 0.03 | 0.05 | 0.08 | 0.09 |
| " | 2 | DL-Pyroglutamic acid | | 0.06 | 0.06 | 0.09 | 0.13 |
| " | 3 | Ethyl L-pyroglutamate | | 0.05 | 0.19 | 0.18 | 0.21 |
| " | 4 | Ethyl DL-pyroglutamate | | 0.05 | 0.27 | 0.41 | 0.52 |
| " | 5 | Hexyl L-pyroglutamate | | 0.04 | 0.38 | 0.74 | 0.65 |
| " | 6 | Hexyl DL-pyroglutamate | | 0.09 | 0.23 | 0.68 | 0.44 |
| " | 7 | Heptyl L-pyroglutamate | | 0.08 | 0.41 | 0.89 | 0.87 |
| " | 8 | Heptyl DL-pyroglutamate | | 0.08 | 0.40 | 0.78 | 0.68 |
| " | 9 | Heptadecyl L-pyroglutamate | | 0.12 | 0.39 | 0.75 | 0.71 |
| " | 10 | Heptadecyl DL-pyroglutamate | | 0.08 | 0.41 | 0.79 | 0.58 |
| " | 11 | Octadecyl L-pyroglutamate | | 0.09 | 0.25 | 0.61 | 0.53 |
| " | 12 | Octadecyl DL-pyroglutamate | | 0.13 | 0.27 | 0.35 | 0.44 |
| " | 13 | Eicosanyl L-pyroglutamate | | 0.03 | 0.10 | 0.09 | 0.08 |
| " | 14 | Eicosanyl DL-pyroglutamate | | 0.07 | 0.35 | 0.44 | 0.46 |
| " | 15 | None | | 0.02 | 0.04 | 0.06 | 0.04 |
| Example | 11 | Compound | (222) | 0.60 | 1.43 | 2.11 | 1.41 |
| " | 12 | " | (224) | 0.71 | 1.78 | 2.24 | 1.36 |
| " | 13 | " | (308) | 0.59 | 1.66 | 1.98 | 1.72 |
| " | 14 | " | (310) | 0.63 | 1.86 | 2.50 | 1.59 |

TABLE 2

| | | Penetration enhancer | | Concentration of nifedipine in the blood (ng/ml) | | | |
|---|---|---|---|---|---|---|---|
| | | | | 3 hrs. | 6 hrs. | 9 hrs. | 24 hrs. |
| Example | 15 | Compound | (112) | 43 | 67 | 35 | 32 |

TABLE 2-continued

|  |  | Penetration enhancer | Concentration of nifedipine in the blood (ng/ml) | | | |
|---|---|---|---|---|---|---|
|  |  |  | 3 hrs. | 6 hrs. | 9 hrs. | 24 hrs. |
| " | 16 | " (114) | 39 | 49 | 52 | 29 |
| " | 17 | " (116) | 55 | 70 | 43 | 30 |
| " | 18 | " (118) | 41 | 39 | 38 | 31 |
| " | 19 | " (120) | 56 | 48 | 29 | 30 |
| " | 20 | " (102) | 42 | 58 | 29 | 28 |
| " | 21 | " (104) | 37 | 39 | 40 | 24 |
| " | 22 | " (106) | 52 | 62 | 40 | 29 |
| " | 23 | " (108) | 42 | 29 | 27 | 27 |
| " | 24 | " (110) | 43 | 38 | 35 | 31 |
| " | 25 | " (220) | 36 | 49 | 33 | 23 |
| " | 26 | " (132) | 41 | 61 | 41 | 29 |
| " | 27 | " (308) | 44 | 68 | 48 | 24 |
| " | 28 | " (310) | 33 | 49 | 29 | 27 |
| Comparison | 16 | L-Pyroglutamic acid | 6 | 8 | 10 | 7 |
| " | 17 | DL-Pyroglutamic acid | 10 | 11 | 15 | 9 |
| " | 18 | Ethyl L-pyroglutamate | 7 | 7 | 15 | 12 |
| " | 19 | Ethyl DL-pyroglutamate | 8 | 12 | 11 | 12 |
| " | 20 | Hexyl L-pyroglutamate | 9 | 10 | 12 | 9 |
| " | 21 | Hexyl DL-pyroglutamate | 8 | 9 | 10 | 8 |
| " | 22 | Heptyl L-pyroglutamate | 9 | 12 | 16 | 15 |
| " | 23 | Heptyl DL-pyroglutamate | 9 | 10 | 8 | 9 |
| " | 24 | Heptadecyl L-pyroglutamate | 8 | 6 | 9 | 11 |
| " | 25 | Heptadecyl DL-pyroglutamate | 10 | 11 | 7 | 9 |
| " | 26 | Octadecyl L-pyroglutamate | 8 | 7 | 10 | 10 |
| " | 27 | Octadecyl DL-pyroglutamate | 11 | 10 | 12 | 9 |
| " | 28 | Eicosanyl L-pyroglutamate | 10 | 9 | 12 | 9 |
| " | 29 | Eicosanyl DL-pyroglutamate | 9 | 7 | 9 | 7 |
| " | 30 | 2-Hydroxy-3-oleoyloxy-1-pyroglutamyloxypropane | 19 | 28 | 19 | 17 |
| " | 31 | None | 7 | 12 | 10 | 6 |

EXAMPLES 29–42

An ointment was prepared from 5 parts of isosorbide dinitrate, 10 parts of each of the various pyroglutamates shown in Table 3 (Examples 29 to 42), and 85 parts of a gel ointment base (composed of 1 part of Carbopol 934, 12 parts of propylene glycol, 30 parts of ethanol, 1 part of diisopropanolamine and 56 parts of water). The hair in the abdomen of each rat (body weight about 250 g) was removed by an electric hair clipper, and 100 mg of the resulting ointment was coated by a finger tip on a circular area having a diameter of 4 cm on the abdomen. After the lapse of a certain period of time, the blood was drawn from the tail portion of the rat, and the concentration of isosorbide dinitrate in the blood was periodically determined by high performance liquid chromatography.

For comparison, ointments composed of 5 parts of isosorbide dinitrate, 10 parts of the various pyroglutamates shown in Table 3 (Comparisons 32 to 44) and 85 parts of the gel ointment base, and an ointment (Comparison 45) composed of 5 parts of isoborbide dinitrate and 95 parts of the gel ointment base without the inclusion of the pyroglutamate were prepared. These comparative ointments were applied to the abdomens of rats, and the concentration of isosorbide dinitrate in the blood was measured, in the same way as above.

The results are shown in Table 3. It is seen that the absorption of isosorbide dinitrate from the ointments of Examples 29 to 42 (the compositions of this invention) was better than the comparative ointments. During the application of the comositions of this invention and the other ointments, no change in the skin such as erythema was observed at the site of administration.

TABLE 3

|  |  | Penetration enhancer | Concentration of isosorbide dinitrate in the blood (ng/ml) | | | |
|---|---|---|---|---|---|---|
|  |  |  | 3 hrs. | 6 hrs. | 9 hrs. | 24 hrs. |
| Example | 29 | Compound (112) | 1.0 | 2.9 | 3.0 | 1.8 |
| " | 30 | " (114) | 0.9 | 2.8 | 3.3 | 2.5 |
| " | 31 | " (116) | 1.0 | 3.6 | 3.3 | 2.0 |
| " | 32 | " (118) | 1.1 | 3.5 | 3.2 | 2.2 |
| " | 33 | " (120) | 0.9 | 2.3 | 2.9 | 2.2 |
| " | 34 | " (102) | 0.7 | 2.4 | 2.2 | 1.7 |
| " | 35 | " (104) | 0.8 | 2.2 | 1.9 | 1.8 |
| " | 36 | " (106) | 1.0 | 3.4 | 2.9 | 1.8 |
| " | 37 | " (108) | 0.7 | 2.3 | 2.2 | 2.3 |
| " | 38 | " (110) | 0.9 | 3.0 | 2.4 | 1.5 |
| " | 39 | " (220) | 1.3 | 3.1 | 3.0 | 1.5 |
| " | 40 | " (224) | 1.0 | 3.3 | 2.9 | 1.7 |
| " | 41 | " (134) | 0.8 | 2.9 | 3.1 | 2.0 |
| " | 42 | " (310) | 0.9 | 2.8 | 2.7 | 1.8 |
| Comparison | 32 | L-Pyroglutamic acid | 0.6 | 0.7 | 0.8 | 0.7 |
| " | 33 | Ethyl L-pyroglutamate | 0.5 | 1.0 | 0.5 | 0.4 |
| " | 34 | Ethyl DL-pyroglutamate | 0.6 | 0.7 | 0.8 | 0.7 |
| " | 35 | Hexyl L-pyroglutamate | 0.4 | 0.8 | 0.8 | 0.8 |
| " | 36 | Hexyl DL-pyroglutamate | 0.6 | 0.4 | 0.9 | 0.7 |
| " | 37 | Heptyl L-pyroglutamate | 0.7 | 1.1 | 0.9 | 1.2 |

TABLE 3-continued

| | | Penetration enhancer | Concentration of isosorbide dinitrate in the blood (ng/ml) | | | |
|---|---|---|---|---|---|---|
| | | | 3 hrs. | 6 hrs. | 9 hrs. | 24 hrs. |
| " | 38 | Heptyl DL-pyroglutamate | 0.7 | 0.9 | 0.8 | 0.5 |
| " | 39 | Heptadecyl L-pyroglutamate | 0.6 | 0.7 | 0.9 | 1.3 |
| " | 40 | Heptadecyl DL-pyroglutamate | 0.6 | 0.6 | 0.6 | 0.6 |
| " | 41 | Octadecyl L-pyroglutamate | 0.5 | 0.6 | 0.7 | 0.9 |
| " | 42 | Octadecyl DL-pyroglutamate | 0.1 | 0.5 | 0.2 | 0.4 |
| " | 43 | Eicosanyl L-pyroglutamate | 0.4 | 0.6 | 0.7 | 0.6 |
| " | 44 | Eicosanyl DL-pyroglutamate | 0.3 | 0.6 | 0.4 | 0.5 |
| " | 45 | None | 0.5 | 0.6 | 0.6 | 0.6 |

EXAMPLES 43-56

An ointment was prepared from 1 part of propranolol hydrochloride, 10 parts of each of the various pyroglutamates shown in Table 4 (Examples 15 to 28), and 89 parts of a gel ointment base (composed of 1 part of Carbopol 934, 12 parts of propylene glycol, 30 parts of ethanol, 1 part of diisopropanolamine and 56 parts of water). The hair in the abdomen of each rat (body weight about 250 g) was removed by an electric hair clipper, and 100 mg of the resulting ointment was coated by a finger tip on a circular area having a diameter of 4 cm on the abdomen. After the lapse of a certain period of time, the blood was drawn from the tail portion of the rat, and the concentration of nifedipine in the blood was periodically determined by high performance liquid chromatography (fluorescent detector).

For comparison, ointments composed of 1 part of propranolol hydrochloride, 10 parts of the various pyroglutamates shown in Table 4 (Comparisons 46 to 59) and 89 parts of the gel ointment base, and an ointment (Comparison 60) composed of 1 part of propranolol hydrochloride and 99 parts of the gel ointment base without the inclusion of the pyroglutamate were prepared. These comparative ointments were applied to the abdomens of rats, and the concentration of propranolol hydrochloride in the blood was measured, in the same way as above.

The results are shown in Table 4. It is seen that the absorption of propranolol hydrochloride from the ointments of Examples 43 to 56 (the compositions of this invention) was better than the comparative ointments. During the application of the compositions of this invention and the other ointments, no change in the skin such as erythema was observed at the site of administration.

TABLE 4

| | | Penetration enhancer | | Concentration of propranolol hydrochloride in the blood (ng/ml) | | | |
|---|---|---|---|---|---|---|---|
| | | | | 3 hrs. | 6 hrs. | 9 hrs. | 24 hrs. |
| Example | 43 | Compound | (112) | 6.3 | 15.4 | 13.2 | 5.8 |
| " | 44 | " | (114) | 6.8 | 13.7 | 14.5 | 7.0 |
| " | 45 | " | (116) | 8.1 | 14.2 | 13.9 | 6.4 |
| " | 46 | " | (118) | 7.6 | 10.8 | 15.1 | 5.0 |
| " | 47 | " | (120) | 6.7 | 14.4 | 14.2 | 10.0 |
| " | 48 | " | (102) | 5.9 | 13.8 | 13.0 | 6.1 |
| " | 49 | " | (104) | 6.5 | 12.8 | 14.4 | 5.3 |
| " | 50 | " | (106) | 7.9 | 13.8 | 14.1 | 3.8 |
| " | 51 | " | (108) | 6.7 | 10.5 | 9.8 | 9.2 |
| " | 52 | " | (110) | 4.7 | 12.2 | 13.6 | 10.1 |
| " | 53 | " | (220) | 3.8 | 9.6 | 14.1 | 8.9 |
| " | 54 | " | (224) | 6.0 | 13.9 | 12.3 | 7.5 |
| " | 55 | " | (308) | 5.9 | 14.3 | 14.4 | 8.0 |
| " | 56 | " | (310) | 7.2 | 14.7 | 10.3 | 6.2 |
| Comparison | 46 | L-Pyroglutamic acid | | 0.9 | 3.5 | 3.1 | 0.8 |
| " | 47 | DL-Pyroglutamic acid | | 1.1 | 4.0 | 2.7 | 0 |
| " | 48 | Ethyl L-pyroglutamate | | 1.2 | 3.3 | 1.0 | 0 |
| " | 49 | Ethyl DL-pyroglutamate | | 1.1 | 0.9 | 3.6 | 0.7 |
| " | 50 | Hexyl L-pyroglutamate | | 1.2 | 4.5 | 2.9 | 0.5 |
| " | 51 | Hexyl DL-pyroglutamate | | 1.0 | 5.4 | 4.4 | 1.2 |
| " | 52 | Heptyl L-pyroglutamate | | 1.3 | 5.8 | 5.7 | 2.9 |
| " | 53 | Heptyl DL-pyroglutamate | | 1.4 | 4.8 | 3.8 | 0 |
| " | 54 | Heptadecyl L-pyroglutamate | | 1.9 | 6.0 | 3.2 | 0.8 |
| " | 55 | Heptadecyl DL-pyroglutamate | | 1.5 | 3.7 | 3.9 | 4.4 |
| " | 56 | Octadecyl L-pyroglutamate | | 0.8 | 1.9 | 4.2 | 0.8 |
| " | 57 | Octadecyl DL-pyroglutamate | | 1.3 | 0.5 | 1.7 | 1.6 |
| " | 58 | Eicosanyl L-pyroglutamate | | 0 | 0.9 | 1.3 | 0 |
| " | 59 | Eicosanyl DL-pyroglutamate | | 0 | 0 | 1.2 | 0.8 |
| " | 60 | None | | 1.0 | 2.5 | 2.1 | 0.2 |

EXAMPLES 57-70

An ointment was prepared from 0.15 part of betamethasone valerate, 9.85 parts of each of the pyroglutamates shown in Table 5 (Examples 57 to 70), and 90 parts of the gel ointment base. The carrageenan-induced edema inhibiting effect of the ointment was examined in accordance with the method of E. Passarella [Arzneim, Forsch. 30 (I), No. 4, pages 647–651 (1980)]. Specifically, 0.1 ml of a 1% carrageenan suspension in 0.9% NaCl solution was injected into the tip of the right paw of each rat (body weight 150–175 g). The volume of the paw was measured before the administation of carrageenan and 3, 5 and 6 hours after the carrageenan administration by a mercury displacement device. The ointment was well rubbed into the inflamed site in an amount of 100 mg.

For comparision, ointments composed of 0.15 parts of betamethasone, 9.85 parts of the various pyroglutamates indicated in Table 5 (Comparisons 61 to 74) and 90 parts of the gel ointment base, an ointment (Comparison 75) composed of 0.15 part of betamethasone valerate and 99.85 parts of the gel ointment base, and an ointment composed only of the gel ointment base were prepared. These ointments were applied to the tip of the paw, and their edema inhibiting effects were examined.

The percent edema inhibitions were calculated on the basis of the edema formation ratio of a rat to which only the gel ointment base was administered. The results are summarized in Table 5.

TABLE 5

|  | Penetration enhancer | Edema inhibition (%) | | |
|---|---|---|---|---|
|  |  | 3 hrs. | 6 hrs. | 9 hrs. |
| Example 57 | Compound (112) | 18.6 | 38.9 | 37.4 |
| Example 58 | Compound (114) | 20.2 | 38.5 | 37.3 |
| Example 59 | Compound (116) | 19.8 | 40.2 | 40.3 |
| Example 60 | Compound (118) | 20.0 | 38.5 | 36.8 |
| Example 61 | Compound (120) | 17.8 | 38.5 | 39.6 |
| Example 62 | Compound (102) | 16.3 | 39.7 | 38.3 |
| Example 63 | Compound (104) | 20.3 | 40.1 | 35.4 |
| Example 64 | Compound (106) | 17.4 | 40.1 | 40.0 |
| Example 65 | Compound (108) | 18.8 | 35.3 | 38.1 |
| Example 66 | Compound (110) | 17.4 | 38.0 | 38.6 |
| Example 67 | Compound (220) | 18.3 | 37.7 | 36.9 |
| Example 68 | Compound (224) | 19.5 | 38.8 | 38.5 |
| Example 69 | Compound (308) | 17.0 | 38.0 | 40.2 |
| Example 70 | Compound (310) | 17.0 | 39.4 | 40.2 |
| Comparison 61 | L-Pyroglutamic acid | 10.3 | 11.2 | 16.3 |
| Comparison 62 | DL-Pyroglutamic acid | 10.8 | 11.4 | 15.2 |
| Comparison 63 | Ethyl L-pyroglutamate | 10.4 | 12.7 | 17.2 |
| Comparison 64 | Ethyl DL-pyroglutamate | 9.5 | 10.2 | 12.1 |
| Comparison 65 | Hexyl L-pyroglutamate | 10.0 | 11.5 | 13.8 |
| Comparison 66 | Hexyl DL-pyroglutamate | 11.2 | 11.5 | 11.0 |
| Comparison 67 | Heptyl L-pyroglutamate | 9.3 | 12.8 | 13.7 |
| Comparison 68 | Heptyl DL-pyroglutamate | 10.7 | 10.9 | 9.5 |

TABLE 5-continued

|  | Penetration enhancer | Edema inhibition (%) | | |
|---|---|---|---|---|
|  |  | 3 hrs. | 6 hrs. | 9 hrs. |
| Comparison 69 | Heptadecyl L-pyroglutamate | 11.2 | 10.6 | 16.5 |
| Comparison 70 | Heptadecyl DL-pyroglutamate | 10.5 | 12.8 | 14.8 |
| Comparison 71 | Octadecyl L-pyroglutamate | 10.0 | 11.4 | 14.4 |
| Comparison 72 | Octadecyl DL-pyroglutamate | 9.6 | 13.0 | 15.6 |
| Comparison 73 | Eicosanyl L-pyroglutamate | 9.3 | 10.5 | 15.6 |
| Comparison 74 | Eicosanyl DL-pyroglutamate | 9.2 | 11.1 | 16.7 |
| Comparison 75 | None | 9.2 | 10.4 | 15.5 |

EXAMPLES 71–84

Cacao butter (93 parts) and 7 parts of each of the various pyroglutamates shown in Table 6 were uniformly mixed. (Asu$^{1.7}$)-eel calcitonin was gradually added and mixed with the mixture to form a uniform composition. The composition was slightly warmed, and filled into a suppository container to form a suppository for rats having a diameter of about 3 mm and a length of about 8 mm. This suppository contained 0.7 MRC unit of calcitonin. The suppository was intrarectally administered to a rat, and the concentration of calcium in the blood serum after administration was measured by using a calcium measuring kit (made by Iatoron Co.).

For comparison, suppositories (Comparisons 76 to 87) composed of 93 parts of cacao butter, 7 parts of the various pyroglutamates shown in Table 6 and caltitonin and a suppository composed only of cacao butter and caltitonin (Comparison 88) were prepared. They wre individually administered intrarectally to rats, and the calcium concentration in the serum was measured.

The results are shown in Table 6. It is seen that the absorption of caltitonin from the suppositories of Examples 71 to 84 was better than that from the comparative suppositories.

TABLE 6

|  |  | Penetration enhancer |  | Percent decrease of the serum calcium level from that before administration (%) | | | |
|---|---|---|---|---|---|---|---|
|  |  |  |  | 1 hr. | 2 hrs. | 3 hrs. | 5 hrs. |
| Example | 71 | Compound | (112) | 29.7 | 26.6 | 15.9 | 0.6 |
| " | 72 | " | (114) | 33.4 | 25.1 | 10.3 | 0.9 |
| " | 73 | " | (116) | 35.1 | 27.4 | 16.8 | 1.1 |
| " | 74 | " | (118) | 32.6 | 24.7 | 10.8 | 1.2 |
| " | 75 | " | (120) | 26.2 | 20.5 | 18.1 | 0.5 |
| " | 76 | " | (102) | 28.4 | 24.1 | 14.8 | 0.7 |
| " | 77 | " | (104) | 30.1 | 20.4 | 11.6 | 0.9 |
| " | 78 | " | (106) | 30.4 | 27.2 | 15.9 | 1.0 |
| " | 79 | " | (108) | 31.2 | 23.3 | 11.6 | 1.0 |
| " | 80 | " | (110) | 26.2 | 18.9 | 10.5 | 0.9 |
| " | 81 | " | (220) | 28.3 | 25.1 | 10.8 | 1.0 |
| " | 82 | " | (224) | 29.2 | 26.7 | 11.4 | 0.9 |
| " | 83 | " | (308) | 27.5 | 26.3 | 12.0 | 0.9 |
| " | 84 | " | (310) | 26.7 | 20.2 | 12.0 | 0.7 |
| Comparison | 76 | Ethyl L-pyroglutamate | | 4.8 | 2.1 | 0.8 | 0.7 |
| " | 77 | Ethyl DL-pyroglutamate | | 6.3 | 2.0 | 0.9 | 0.8 |
| " | 78 | Hexyl L-pyroglutamate | | 5.1 | 1.9 | 0.7 | 0.8 |
| " | 79 | Hexyl DL-pyroglutamate | | 7.5 | 2.0 | 0.8 | 0.8 |
| " | 80 | Heptyl L-pyroglutamate | | 10.1 | 3.0 | 0.9 | 0.7 |
| " | 81 | Heptyl DL-pyroglutamate | | 10.0 | 2.8 | 0.9 | 1.2 |
| " | 82 | Heptadecyl L-pyroglutamate | | 7.5 | 2.3 | 0.9 | 0.8 |
| " | 83 | Heptadecyl DL-pyroglutamate | | 6.7 | 2.9 | 0.9 | 1.3 |
| " | 84 | Octadecyl L-pyroglutamate | | 4.4 | 2.2 | 0.8 | 0.5 |
| " | 85 | Octadecyl DL-pyroglutamate | | 4.1 | 1.8 | 0.8 | 0.8 |
| " | 86 | Eicosanyl L-pyroglutamate | | 3.6 | 2.0 | 0.8 | 0.8 |
| " | 87 | Eicosanyl DL-pyroglutamate | | 3.6 | 2.4 | 0.9 | 0.9 |

TABLE 6-continued

| | | Penetration enhancer | Percent decrease of the serum calcium level from that before administration (%) | | | |
|---|---|---|---|---|---|---|
| | | | 1 hr. | 2 hrs. | 3 hrs. | 5 hrs. |
| " | 88 | None | 3.5 | 2.1 | 0.8 | 0.8 |

EXAMPLES 85-98

Fractionated coconut oil (90 parts) and 10 parts of each of the various pyroglutamates indicated in Table 7 were uniformly mixed, and then hog insulin was gradually added to form a uniform dispersion. The dispersion was filled in a gelatin capsule for suppositoes to form a gelatin capsular suppository. The suppository contained 9.6 units of insulin. The suppository was intrarectally administered to a rabbit and the blood glucose level after administration was measured by the glucose oxidase method.

For comparison, suppositories composed of 90 parts of fractionated coconut oil, 10 parts of the various pyroglutamates indicated in Table 7 (Comparisons 89 to 102) and insulin, and a suppository composed only of fractionated coconut oil and insulin (Comparison 103) were prepared, and tested in the same way as above.

The results obtained are shown in Table 7. It is seen that the absorption of insulin from the suppositories (Examples 85 to 98) was better than that from the comparative suppository.

EXAMPLES 99-112

Cacao butter (80 parts), 10 parts of each of the pyroglumtamates indicated in Table 8, and 10 parts of cephalothin sodium were uniformly mixed and then slightly warmed. The mixture was filled in a suppository container to form a suppository containing 1 g of the mixture. The suppository was administered intrarectally to a Beagle dog, and the concentration of cephalothin sodium in the blood after administration was measured by the cup method.

For comparison, suppositories composed of 10 parts of the various pyroglutamates indicated in Table 8 (Comparisons 104 to 111), 80 parts of cacao butter, 10 parts of the various pyroglutamates indicated in Table 8 and 10 parts of cephalothin sodium, and a suppository composed of 90 parts of cacao butter and 10 parts of cephalothin (Comparison 112) were prepared. These suppositories were individually administered intrarectally to Beagle dogs, and the concentration of cephalothin sodium in the blood was measured.

The results obtained are shown in Table 8. It is seen that the absorption of cephalothin sodium from the suppositories in accordance with the invention (Examples 99 to 112) was better than that from the comparative suppositories.

TABLE 7

| | | Penetration enhancer | | Percent decrease of the blood glucose level from that before administration (%) | | | |
|---|---|---|---|---|---|---|---|
| | | | | 30 min. | 1 hr. | 2 hrs. | 3 hrs. |
| Example | 85 | Compound | (112) | 28.4 | 27.7 | 18.8 | 0.9 |
| " | 86 | " | (114) | 29.8 | 28.6 | 20.1 | 0.5 |
| " | 87 | " | (116) | 38.1 | 39.4 | 20.1 | 5.4 |
| " | 88 | " | (118) | 33.1 | 28.5 | 19.4 | 1.2 |
| " | 89 | " | (120) | 27.6 | 28.2 | 20.0 | −0.8 |
| " | 90 | " | (102) | 27.5 | 24.4 | 17.9 | 1.0 |
| " | 91 | " | (104) | 21.4 | 22.6 | 21.1 | −0.1 |
| " | 92 | " | (106) | 35.1 | 34.3 | 19.0 | 5.5 |
| " | 93 | " | (108) | 22.2 | 27.4 | 19.6 | 1.6 |
| " | 94 | " | (110) | 26.6 | 19.8 | 21.1 | −0.9 |
| " | 95 | " | (220) | 25.3 | 25.2 | 16.2 | 1.0 |
| " | 96 | " | (224) | 29.2 | 32.1 | 18.5 | 3.1 |
| " | 97 | " | (308) | 30.7 | 26.5 | 19.1 | 3.0 |
| " | 98 | " | (310) | 28.5 | 24.3 | 17.6 | 2.7 |
| Comparison | 89 | L-Pyroglutamic acid | | 1.3 | 0.7 | 0.6 | 0.1 |
| " | 90 | DL-Pyroglutamic acid | | −0.8 | 0.9 | 0.6 | −0.5 |
| " | 91 | Ethyl L-pyroglutamate | | 3.1 | 1.4 | 0.7 | 0.3 |
| " | 92 | Ethyl DL-pyroglutamate | | 1.3 | −0.1 | 0.3 | 0.0 |
| " | 93 | Hexyl L-pyroglutamate | | 4.3 | 1.2 | 0.8 | 0 |
| " | 94 | Hexyl DL-pyroglutamate | | 4.3 | 1.1 | 1.0 | −0.9 |
| " | 95 | Heptyl L-pyroglutamate | | 7.1 | 0.7 | 0.5 | −1.1 |
| " | 96 | Heptyl DL-pyroglutamate | | 10.2 | 0.9 | 0.9 | 0.9 |
| " | 97 | Heptadecyl L-pyroglutamate | | 5.5 | 4.4 | 0.9 | −1.2 |
| " | 98 | Heptadecyl DL-pyroglutamate | | 5.5 | 2.4 | 0.9 | 0.2 |
| " | 99 | Octadecyl L-pyroglutamate | | 2.5 | 3.3 | 1.6 | 0.1 |
| " | 100 | Octadecyl DL-pyroglutamate | | −0.9 | 0.7 | 1.1 | 0.6 |
| " | 101 | Eicosanyl L-pyroglutamate | | −0.1 | 0.7 | 0.6 | −1.0 |
| " | 102 | Eicosanyl DL-pyroglutamate | | −0.9 | 0.6 | 0.7 | −0.5 |
| " | 103 | None | | −0.9 | 0.8 | 0.7 | −1.1 |

TABLE 8

| Penetration enhancer | | | | Concentration of cephalothin sodium in the blood (μg/ml) | | | |
|---|---|---|---|---|---|---|---|
| | | | | 1 hr. | 3 hrs. | 5 hrs. | 7 hrs. |
| Example | 99 | Compound | (112) | 0.5 | 0.5 | 0.2 | 0 |
| " | 100 | " | (114) | 0.4 | 0.4 | 0 | 0 |
| " | 101 | " | (116) | 0.6 | 0.6 | 0.6 | 0.2 |
| " | 102 | " | (118) | 0.5 | 0.7 | 0.3 | 0.1 |
| " | 103 | " | (120) | 0.5 | 0.6 | 0.4 | 0.2 |
| " | 104 | " | (102) | 0.4 | 0.5 | 0.3 | 0.1 |
| " | 105 | " | (104) | 0.2 | 0.6 | 0.5 | 0.2 |
| " | 106 | " | (106) | 0.7 | 0.7 | 0.7 | 0.4 |
| " | 107 | " | (108) | 0.5 | 0.3 | 0.5 | 0 |
| " | 108 | " | (110) | 0.4 | 0.3 | 0.2 | 0.1 |
| " | 109 | " | (220) | 0.3 | 0.4 | 0.4 | 0.1 |
| " | 110 | " | (224) | 0.3 | 0.4 | 0.3 | 0 |
| " | 111 | " | (308) | 0.5 | 0.6 | 0.6 | 0 |
| " | 112 | " | (310) | 0.5 | 0.5 | 0.4 | 0.1 |
| Comparison | 104 | L-Pyroglutamic acid | | 0 | 0 | 0 | 0 |
| " | 105 | DL-Pyroglutamic acid | | 0 | 0 | 0 | 0 |
| " | 106 | Ethyl L-pyroglutamate | | 0 | 0 | 0 | 0 |
| " | 107 | Ethyl DL-pyroglutamate | | 0 | 0 | 0 | 0 |
| " | 108 | Hexyl L-pyroglutamate | | 0 | 0 | 0 | 0 |
| " | 109 | Hexyl DL-pyroglutamate | | 0 | 0 | 0 | 0 |
| " | 110 | Eicosanyl L-pyroglutamate | | 0 | 0 | 0 | 0 |
| " | 111 | Eicosanyl DL-pyroglutamate | | 0 | 0 | 0 | 0 |
| " | 112 | None | | 0 | 0 | 0 | 0 |

EXAMPLES 113-126

Ten parts of each of the pyrogluamates shown in Table 9 (Examples 113 to 126) was mixed uniformly with 90 parts of distilled water, and then (Asu$^{1.7}$)-eel calcitonin was gradually added to form a uniform composition as a nasal drop. This nasal drop contained 15 units/50 microliters of calcitonin. The nasal drop in a dose of 50 microliters was administered to the nasal cavity of a New Zealand rabbit (clean). The calcium concentration in the serum after administration was measured by using a calcium measuring kit (Iatoron Co.).

For comparison, liquid preparations composed of 10 parts of each of the pyroglutamates indicated in Table 9 (Examples 113 to 126), 90 parts of distilled water and caltitonin and a liquid preparation composed only of distilled water and calcitonin (Comparison 127) were prepared. They were individually administered to the nasal cavity of a rabbit, and the concentration of calcium in the serum was measured.

The results are shown in Table 9. It is seen that the absorption of calcitonin from the nasal liquid preparations of Examples 113 to 126 was better than that from the comparative nasal liquid preparations.

TABLE 9

| | | Penetration enhancer | | Percent decrease of the serum calcium level from that before administration (%) | | | |
|---|---|---|---|---|---|---|---|
| | | | | 1 hr. | 2 hrs. | 3 hrs. | 5 hrs. |
| Example | 113 | Compound | (112) | 8.1 | 6.0 | 1.8 | 0 |
| " | 114 | " | (114) | 8.1 | 7.5 | 3.8 | 0.2 |
| " | 115 | " | (116) | 7.5 | 5.3 | 2.4 | 0.8 |
| " | 116 | " | (118) | 6.5 | 7.0 | 3.4 | 0.6 |
| " | 117 | " | (120) | 7.6 | 6.1 | 3.0 | 0.9 |
| " | 118 | " | (102) | 5.1 | 3.9 | 3.1 | 0.5 |
| " | 119 | " | (104) | 7.0 | 7.2 | 2.9 | |
| " | 120 | " | (106) | 6.5 | 6.0 | 2.8 | 0.7 |
| " | 121 | " | (108) | 8.1 | 0.4 | 2.8 | 1.0 |
| " | 122 | " | (110) | 6.6 | 6.1 | 3.0 | 0 |
| " | 123 | " | (220) | 7.7 | 5.9 | 1.9 | 0 |
| " | 124 | " | (224) | 9.0 | 6.3 | 2.2 | 0.6 |
| " | 125 | " | (308) | 6.5 | 5.4 | 2.7 | 0.6 |
| " | 126 | " | (310) | 5.3 | 4.8 | 1.6 | 0.4 |
| Comparison | 113 | L-Pyroglutamic acid | | 1.9 | 0.7 | 0 | 0 |
| " | 114 | DL-Pyroglutamic acid | | 2.0 | 1.0 | 0 | 0 |
| " | 115 | Ethyl L-pyroglutamate | | 1.0 | 0.8 | 0 | 0 |
| " | 116 | Ethyl DL-pyroglutamate | | 1.8 | 0.9 | 0 | 0 |
| " | 117 | Hexyl L-pyroglutamate | | 1.9 | 0.8 | 0.1 | 0 |
| " | 118 | Hexyl DL-pyroglutamate | | 0.9 | 1.1 | 0 | 0 |
| " | 119 | Heptyl L-pyroglutamate | | 2.1 | 1.0 | 0.5 | 0 |
| " | 120 | Heptyl DL-pyroglutamate | | 0.9 | 1.3 | 0.6 | 0.1 |
| " | 121 | Heptadecyl L-pyroglutamate | | 1.5 | 0.8 | 0.2 | 0 |
| " | 122 | Heptadecyl DL-pyroglutamate | | 1.5 | 0.8 | 0.6 | 0 |
| " | 123 | Octadecyl L-pyroglutamate | | 1.6 | 0.7 | 0.1 | 0 |
| " | 124 | Octadecyl DL-pyroglutamate | | 1.5 | 0.8 | 0 | 0 |
| " | 125 | Eicosanyl L-pyroglutamate | | 1.7 | 0.6 | 0 | 0 |
| " | 126 | Eicosanyl DL-pyroglutamate | | 1.2 | 0.9 | 0 | 0 |

TABLE 9-continued

| | Penetration enhancer | Percent decrease of the serum calcium level from that before administration (%) | | | |
|---|---|---|---|---|---|
| | | 1 hr. | 2 hrs. | 3 hrs. | 5 hrs. |
| " | 127 None | 1.8 | 0.6 | 0.1 | 0 |

EXAMPLES 127-145

A diffusion cell was partitioned by an egg shell membrane. A mixed solution consisting of physiological saline containing a drug and dodecyl L-pyroglutamate, and ethyl alcohol (1:1) was filled in the donor side of the cell. The acceptor side of the cell was filled with physiological saline. The two solutions were stirred while maintaining a temperaure of 37° C. After 30 minutes, the amount of the drug diffused from the donor side to the acceptor side was measured.

The diffusion cell was a glass diffusion cell used in an ordinary diffusion experiment. The egg shell membrane was obtained by removing the contents from a raw egg, immersing the shell in 0.7% acetic acid for 30 minutes, subjecting it to ultrasonic treatment for 15 minutes and thereafter carefully peeling the membrane from the shell by fingers. The concentration of the drug in the donor side was adjusted to 0.05%, and the concentration of dodecyl L-pyroglutamate in the donor side, to 1.0%.

As a control, the above experiment was carried out except that only the drug was added to the donor side.

After 30 minutes, the amount of the drug diffused to the acceptor side was measured, and compared with that measured in the control.

The relative amount of permeation of the drug in the system containing the penetration enhancer was determined by taking the amount of the drug permeated in the control as 100. (For the above experimental procedure, reference may be made to M. Washitake et al.: Chem. Pharm. Bull., Vol. 20, page 2855, 1980). The results are shown in Table 10.

TABLE 10

| Example | Drug in the donor side | Relative amount of permeation after 30 minutes |
|---|---|---|
| 127 | Cephatothin | 141 |
| 128 | Griseofulvin | 221 |
| 129 | Indomethacin | 220 |
| 130 | Salicyclic acid | 208 |
| 131 | Piroxicam | 167 |
| 132 | Triamcinolone acetonide | 231 |
| 133 | 5-Fluorouracil | 241 |
| 134 | Procaine | 170 |
| 135 | Estradiol | 203 |
| 136 | Scopolamine | 121 |
| 137 | p-Aminobenzoic acid | 141 |
| 138 | Bupranolol | 164 |
| 139 | Methyldopa | 153 |
| 140 | iso-Sorbide dinitrate | 119 |
| 141 | Diazepam | 157 |
| 142 | Sodium cromoglicate | 168 |
| 143 | Chlorpromazine | 124 |
| 144 | Prostaglandin $F_2$ | 166 |
| 145 | Urokinase | 127 |

EXAMPLE 146

(i) About 10 g of compound (116) was added to 125 g of cacao butter, and they were well mixed by a grinder. Then, 5 g of indomethacin was gradually added and mixed to form a homogeneous composition. The composition was slightly heated to render if flowable, and poured into a container for production of suppositories, followed by solidification at room temperature to obtain solid suppositories for human application each having a weight of 1.4 g. One suppository contained about 0.05 g of indomethacin.

(ii) About 5 g of compound (116) was dispersed in 35 g of fractionated coconut oil, and 10 g of cefaloridine was added. The mixture was well stirred in a mixer to obtain a homogeneous dispersion. 500 mg of the dispersion was filled into a gelatin capsule for suppositories to obtain gelatin capsule suppositories for humans. One capsule contained about 100 mg of cefaloridine.

EXAMPLE 147

One gram of beclomethasone dipropionate and 5 g of compound (116) were added to 1,000 g of hydroxypropyl cellulose. They were mechanically mixed to form a powder having beclomethasone dipropionate uniformed dispersed therein. Fifty milligrams of the powder was filled in a #2 hard gelatin capsule to form a powdery preparation for nasal administration in unit dosage form.

EXAMPLE 148

An ointment for administration to the oral cavity was prepared from 2 parts by weight of compound (116), 2.5 parts by weight of polyethylene (molecular weight about 20,000), 45.5 parts by weight of liquid paraffin, 16.5 parts by weight of gelatin, 165 parts by weight of pectin, 17 parts by weight of carboxymethyl cellulose sodium and 0.1 part by weight of triamcinolone acetonide.

EXAMPLE 149

One part by weight of fluocinolone, 15 parts by weight of cetyl alcohol, 10 parts by weight of propylene glycol, 15 parts by weight of sodium laurylsulfate, 2 parts by weight of compound (116) and 30 parts by weight of water were mixed under heat until the mixture became uniform. Then, the heating was stopped, and the mixture was left to stand. When its temperature returned to room temperature, 25 parts by weight of water was added, and the mixture was stirred until it became uniform. A lotion was obtained.

EXAMPLE 150

A cream was prepared from 1 part by weight of griseofulvin, 12 parts by weight of stearyl alcohol, 0.5 part by weight of cholesterol, 8 parts by weight of white beeswax, 1 part by weight of sorbitan monoleate, 3 parts by weight of Polysorbate 80, 2 parts by weight of compound (116), 1 part by weight of sorbitol, 0.5 part by weight of sodium tartrate and 71 parts by weight of purified water.

What is claimed is:

1. A pharmaceutical composition for external use with the enhanced penetration of a pharmacologically active agent through the skin or mucosa of a warm-blooded animal, said composition comprising
(A) an effective amount of an anti-inflammatory agent selected from the group consisting of salicylic acid, indomethacin, and betamethasone valerate and
(B) an effective amount of an optically active or inactive pyroglutamate of the following formula

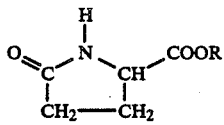
(1)

wherein R represents a linear, branched or cyclic alkyl or alkenyl group having 10 to 14 carbon atoms, as a penetration enhancer.

2. The composition of claim 1 wherein the pyroglutamate is represented by formula (1) in which R is a linear or branched alkyl or alkenyl group having 12 to 14 carbon atoms.

3. The composition of claim 1 wherein the pyroglutamate is represented by formula (1) in which R is a linear or branched alkyl group having 12 carbon atoms.

4. The composition of claim 1 which is in the form of a solution, an emulsion, a suspension, a semi-solid, a powder, a regularly shaped compressed article, or a film.

5. The composition of claim 1 wherein the pharmacologically active agent is salicylic acid.

6. In a method of enhancing the penetration of a pharmacologically active agent through the skin or mucosa of a warm-blooded animal, the improvement which comprises externally applying to the skin or mucosa an effective amount of an optically active or inactive pyroglutamate in an amount sufficient to enhance said penetration, said pyroglutamate having the following formula:

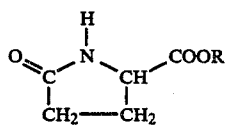
(1)

wherein R represents a linear, branched or cyclic alkyl or alkenyl group having 10 to 14 carbon atoms.

7. A method according to claim 6, wherein the pharmacological agent is an anti-inflammatory agent.

8. A method according to claim 7, wherein the anti-inflammatory agent is selected from the group consisting of salicylic acid, indomethacin and betamethosone valerate.

9. The method of claim 6 wherein the pharmacologically active agent (A) is applied together with the penetration enhancer (B) to the surface of the skin of the warm-blooded animal.

10. The method of claim 6 wherein the pharmacologically active agent is applied together with the penetration enhancer to the surface of the rectal mucosa of the warm-blooded animal.

11. The method of claim 6 wherein the pharmacologically active agent is applied together with the penetration enhancer to the surface of the mucosa of the oral cavity of the warm-blooded animal.

12. The method of claim 6 wherein the pharmacologically active agent is applied together with the penetration enhancer to the surface of the mucosa of the nasal cavity of the warm-blooded animal.

13. The method of any one of claims 6 and 7–10 wherein the pharmacologically active agent and the penetration enhancer are applied in the form of a composition.

14. The method of claim 6 wherein the pharmacologically active agent is an anti-inflammatory agent.

* * * * *